(12) United States Patent
Junghans et al.

(10) Patent No.: US 6,291,685 B1
(45) Date of Patent: Sep. 18, 2001

(54) METHODS FOR THE PREPARATION OF 4-HYDROXYBENZOTHIOPHENE

(75) Inventors: Bernd Junghans, Edingen-Neckarhausen (DE); Michelangelo Scalone, Birsfelden (CH); Thomas Albert Zeibig, Mutterstadt (DE)

(73) Assignee: Hoffmann–La Roche Inc., Nutley, NJ (US)

( * ) Notice: Subject to any disclaimer, the term of this patent is extended or adjusted under 35 U.S.C. 154(b) by 0 days.

(21) Appl. No.: 09/625,887

(22) Filed: Jul. 26, 2000

(30) Foreign Application Priority Data

Aug. 2, 1999 (EP) .................................. 99115222

(51) Int. Cl.$^7$ ................................................ C07D 333/54
(52) U.S. Cl. ................................................................ 549/51
(58) Field of Search ................................................ 549/51

(56) References Cited

U.S. PATENT DOCUMENTS

| | | | |
|---|---|---|---|
| 5,330,998 | * 7/1994 | Clark et al. | 514/369 |
| 5,380,861 | 1/1995 | Scalone et al. | |
| 6,133,279 | * 10/2000 | Cynshi et al. | 514/278 |

FOREIGN PATENT DOCUMENTS

| | | |
|---|---|---|
| WO 94/27995 | 12/1994 | (WO) . |
| WO 98/42704 | 10/1998 | (WO) . |

OTHER PUBLICATIONS

Iwasaki et al., J. Org. Chem. 56, pp. 1922–1927 (1991).
Matsuzaka et al., Org. Chem. 53, pp. 3832–3838 (1988).
Practical Organic Chemistry, A. I. Vogel, Longmans Ed., pp. 390–393 (1967).
Houben–Weyl, "Methoden der organischen Chemie", vol. E1, pp. 106–182, Georg Thieme Verlag Stuttgart (1982).
Aspects Homog. Catal., 4, pp. 145–202 (1981).

* cited by examiner

Primary Examiner—Cecilia Tsang
Assistant Examiner—Sonya N. Wright
(74) Attorney, Agent, or Firm—George W. Johnston; William H. Epstein; F. Aaron Dubberley

(57) ABSTRACT

The present invention is concerned with a novel process for the preparation of the hydroxybenzothiophene of formula I

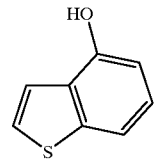

I comprising cyclocarbonylation of a compound of formula II

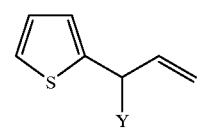

II wherein Y is as defined in the specification, followed by saponification. The compound of Formula I is a building block of pharmaceutically active substances, e.g. 5-[4-[2-(5-methyl-2-phenyl-4-oxazolyl)ethoxy]-7-benzothiophenylmethyl]-2,4-thiazolidinedione and the corresponding sodium salt which are from agents useful in the treatment of diabetes.

11 Claims, No Drawings

METHODS FOR THE PREPARATION OF 4-HYDROXYBENZOTHIOPHENE

BACKGROUND OF THE INVENTION

Methods for the preparation of 4-hydroxybenzothiophene have been described by Iwasaki et al. (1991) J. Org. Chem. 1991. 5, 1922. Here a cyclocarbonylation of a primary allylacetate is performed in presence of a high catalyst loading. Further, this process is characterized by at least five process steps which in part require extreme reaction conditions. Therefore, a simpler more efficient process utilizing less process steps has been long desired.

SUMMARY OF INVENTION

The present invention is concerned with a novel process for the preparation of benzothiophene derivatives, especially with the preparation of 4-hydroxybenzothiophene. 4-Hydroxybenzothiophene is a building block for pharmaceutically active compounds, e.g. 5-[4-[2-(5-methyl-2-phenyl-4-oxazolyl)ethoxyl]-7-benzothiophenylmethyl]-2,4-thiazolidinedione. This compound is known in the art and is described for example in International Patent Application WO 94/27995. It is especially useful for prophylaxis and treatment of diabetes mellitus type I and II.

Surprisingly it has been found that using the process according to the present invention 4-hydroxybenzothiophene can be prepared with less process steps under moderate conditions with an outstanding yield.

DETAILED DESCRIPTION

In accordance with this invention, a new procedure is provided for preparing 4-hydroxybenzothiophene having the formula

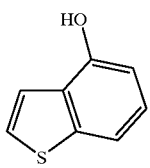

I from a compound of

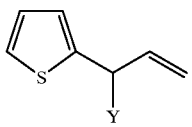

II wherein Y is halogen or —OR; and
—OR is an aryloxy group or a group of formulae —O—(CO)—R', —O—(CO)—O—R", or —O—(PO)—(OR")$_2$, wherein R' is alkyl, perfluoro-$C_{1-20}$-alkyl, aryl, R" is alkyl, aryl or benzyl;

which comprises cyclocarbonylating the compound of formula II by reacting, in an organic solvent medium containing a carboxylic acid anhydride and a base, the compound of formula II with carbon monoxide in the presence of a carbonylation catalyst capable of complexing with carbon monoxide to produce the carboxylic acid ester of the compound of formula I as a reaction product and thereafter saponifying this reaction product to produce the compound of formula I above.

The cyclocarbonylation is carried out by introducing carbon monoxide into the reaction medium containing the compound of formula II above and a carbonylation catalyst capable of complexing with carbon monoxide to produce the carboxylic acid ester of the compound of formula I as a reaction product. The saponification step is carried out after this reaction product is formed. The saponification is carried out by adding a base to the reaction medium so that the pH is raised to any value of from 8 to 14.

Surprisingly, it has been found that using the process of this invention, the 4-hydroxybenzothiophene can be prepared with less process steps under moderate conditions and with an outstanding yield. The process also provides an efficient cyclocarbonylation reaction under mild conditions in a single reaction medium so that the starting material for this reaction, ie., the compound of formula II, does not have to be purified such as by distillation but can be used as crude material. Therefore, this process provides an efficient cyclocarbonylation reaction under mild conditions. In addition, substrates for the cyclocarbonylation reaction (compound of Formula II) do not need to be purified, e.g. by distillation, but can be used as "crude" material.

According to the present invention, the term "cyclocarbonylation" refers to an introduction of a carbonyl group by means of carbon monoxide gas coupled with the formation of a cyclic ring structure.

The term "saponification" refers to the hydrolysis of an ester under basic conditions.

The term "transition metal compound" refers to a metal-phosphine complex compound wherein the term metal refers to Pd, Pt, Ru, Co, Rh or Ni, preferably Pd.

The term "ligand" refers to phosphine, arsine or stibine derivatives, preferable phosphine derivatives, of general formulae $P(R^1)(R^2)(R^3)$, $(R^1)(R^2)P-(X)-P(R^1)(R^2)$, $As(R^1)(R^2)(R^3)$ or $Sb(R^1)(R^2)(R^3)$, preferably $P(R^1)(R^2)(R^3)$, wherein $R^1$, $R^2$, and $R^3$ are below.

The term "alkyl" refers to a branched or straight chain monovalent alkyl radical of one to nine carbon atoms (unless otherwise indicated), preferably one to four (lower) carbon atoms. This term is further exemplified by such radicals as methyl, ethyl, n-propyl, isopropyl, i-butyl, n-butyl, t-butyl and the like.

The term "aryl" refers to a monovalent carbocyclic aromatic radical, e.g. phenyl, optionally substituted, independently, with halogen, lower-alkyl, lower-alkoxy, lower-alkylenedioxy, carboxy, trifluoromethyl and the like, with phenyl being especially preferred.

The term "lower alkanoic acid" refers to those lower alkanoic acids containing from 2 to 6 carbon acids such as propionic acid, acetic acid, etc.

The term "aryloxy", signifies a group of the formula aryl-O— in which the term "aryl" has the significance given above. Phenyloxy is a preferred example of such an aryloxy group.

The term "alkoxy", alone or in combination, signifies a group of the formula alkyl-O— in which the term "alkyl" has the significance given above, such as methoxy, ethoxy, n-propoxy, isopropoxy, n-butoxy, isobutoxy, sec.butoxy and tert.butoxy, preferably methoxy and ethoxy.

The term "alkylenedioxy" refers to $C_{1-3}$-alkyl-dioxy groups, such as methylenedioxy, ethylenedioxy or propylenedioxy.

The term "halogen" refers to fluorine, chlorine, and bromine.

In more detail, the present invention refers to a process for the preparation of compounds of formula I

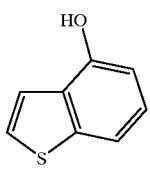

I comprising cyclocarbonylation of a compound of formula II

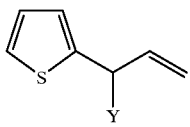

II wherein Y is halogen or —OR;
—OR is an aryloxy group or a group of formulae —O—(CO)—R', —O—(CO)—O—R" or —O—(PO)—(OR")$_2$, wherein R' is alkyl, perfluoro-C$_{1-20}$-alkyl, aryl, R"0 is alkyl, aryl or benzyl;
followed by saponification.

In a preferred embodiment of the invention, the cyclocarbonylation reaction is carried out in the presence of a base and the carbonylation catalyst is a complex of a transition metal compound with a ligand.

In a preferred embodiment of this invention, the cyclocarbonylation reaction carried out in the presence of a base and a carboxylic acid anhydride, one utilizes a catalyst which is a transition metal compound complexed with a ligand. Cyclocarbonylation reactions and their conditions are known. Any of the conventional conditions utilized in such cyclocarbonylation reactions can be utilized in accordance with the process of this invention.

In accordance with the process of this invention, this cyclocarbonylation reaction is carried out in the presence of a carbonylation catalyst capable of complexing with carbon monoxide. Any conventional carbonylation catalyst capable of complexing with carbon monoxide can be utilized in accordance with this invention. Among the preferred catalysts are those catalysts which are transition metal compounds complexed with a ligand. Transition metal compounds useful for the process of the present invention comprise salts of Pd, Pt, Ru, Co, Rh— or Ni and also include transition metals on an inert support such as Pd/C. The use of transition metal compounds as catalysts has been described for example in Matsuzaka et al. (1988) J. Org. Chem. 53, 3832. Preferred transition metal compounds are salts of palladium, e.g. Pd(OAc)$_2$, Pd$_2$dba$_3$, PdCl$_2$, Pd$_2$Cl$_2$($\pi$-allyl)$_2$, PdCl$_2$(NCMe)$_2$, [Pd(NCMe)$_4$] (BF$_4$)$_2$, and most preferably Pd(OAc)$_2$. The mentioned catalysts are known in the art (e.g. U.S. Pat. No. 5,380,861; "Carbonylation, Direct Synthesis of Carbonyl Compounds", H. M. Colquhoun, D. J. Thompson, M. V. Trigg, Plenum Press, 1991) and/or are commercially available (e.g. from Fluka, Buchs, Switzerland or Strem Chemicals, Kehl, Germany).

The ligand of the transition metal compound in the catalyst may be selected from a group consisting of phosphine, arsine or stibine derivatives, preferable phosphine derivatives of general formulae P(R$^1$)(R$^2$)(R$^3$), (R$^1$)(R$^2$)P—(X)—P(R$^1$)(R$^2$), As(R$^1$)(R$^2$)(R$^3$) or Sb(R$^1$)(R$^2$)(R$^3$), preferably P(R$^1$)(R$^2$)(R$^3$), wherein X, R$^1$, R$^2$, and R$^3$ are defined below.

Especially suitable ligands are chiral and non-chiral mono- and diphosphorus compounds for example described in Houben-Weyl, "Methoden der organischen Chemie", vol. E1, page 106 et seq. Georg Thieme Verlag Stuttgart, 1982, and Aspects Homog. Catal., 4, 145–202 (1981), especially those of the formulae P(R$^1$)(R$^2$)(R$^3$) and (R$^1$)(R$^2$)P—(X)—P(R$^1$)(R$^2$)

wherein R$^1$, R$^2$ and R$^3$ each independently are C$_{1-8}$-alkyl, cyclohexyl, benzyl, naphthyl, 2- or 3-pyrrolyl, 2- or 3-furyl, 2- or 3-thiophenyl, 2- or 3- or 4-pyridyl, phenyl or phenyl which is substituted by C$_{1-4}$-aklyl, C$_{1-4}$-alkoxy, halogen, trifluoromethyl, lower alkylydenedioxy or phenyl and X is binaphthyl, 6,6'-dimethyl- or 6,6'-dimethoxybiphenyl-2,2'-diyl, or one of the groups —(CH$_2$)$_n$—, —CH$_2$ CH$_2$—P(C$_6$H$_5$)—CH$_2$ CH$_2$—,

IV

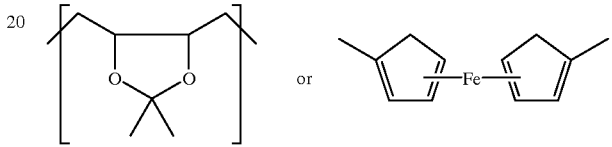

and n is number of 1–8.

Examples of suitable phosphorus ligands are shown in Scheme 1.

Scheme 1

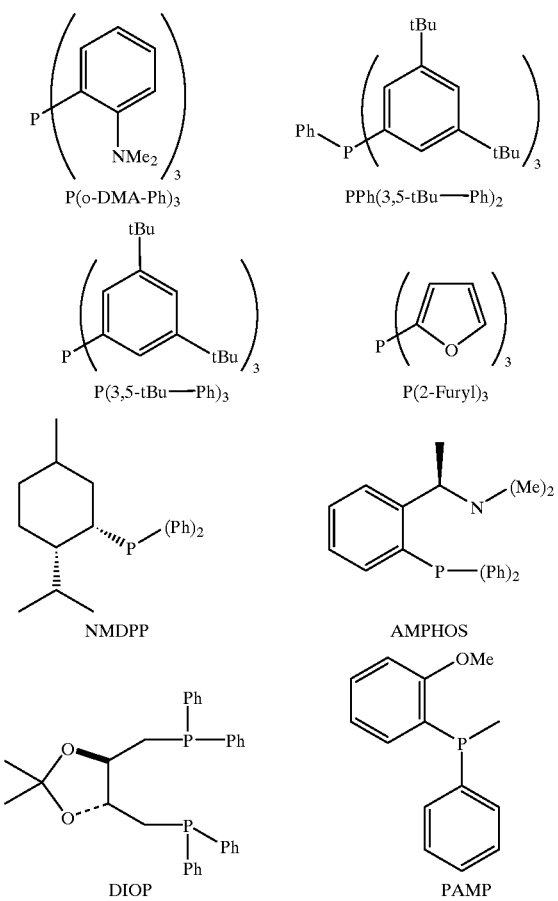

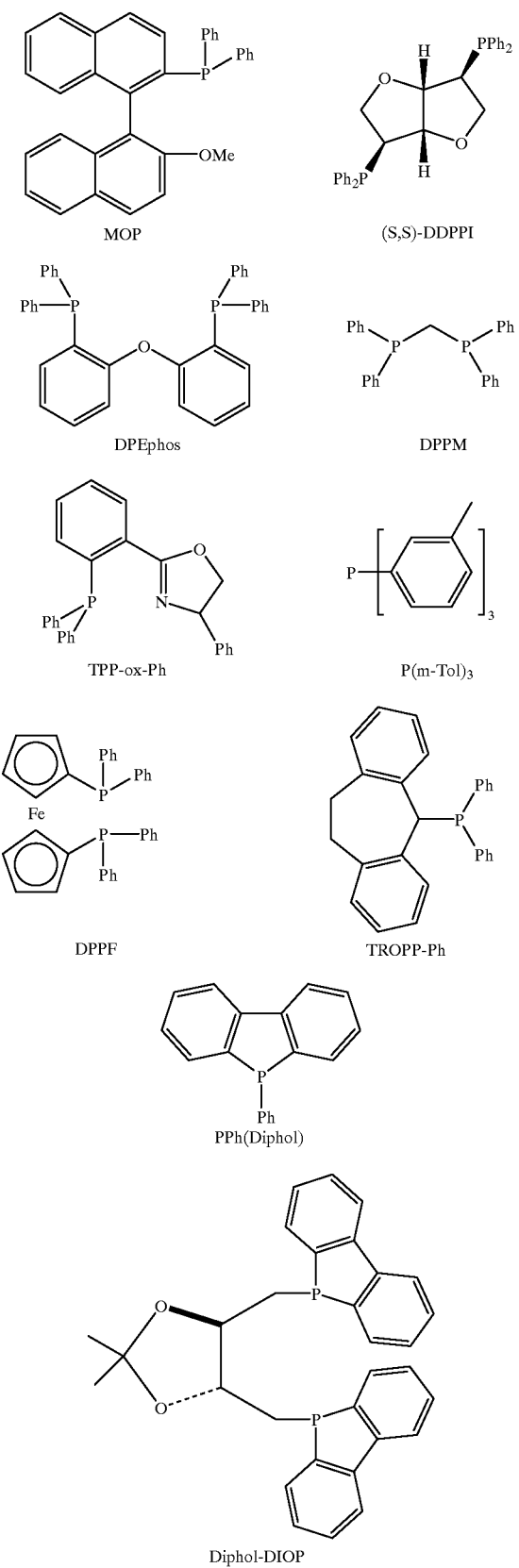

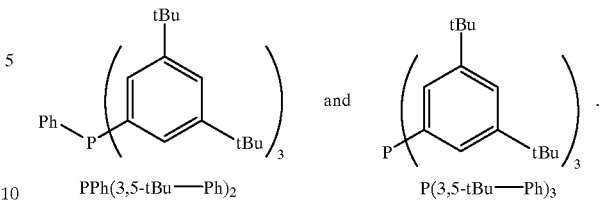

The preparation of a transition metal complex is explained in more detail for the corresponding palladium-phosphine complex: The palladium-phosphine complex compound is conveniently formed in situ from a palladium component and a phosphine ligand. These palladium components is for example metallic palladium, which is optionally supported on a carrier material such as carbon, or a complex or a salt of 0-, 2- or 4-valent palladium such as palladium-bis (dibenzylideneacetone), palladium chloride, palladium acetate and the like. For the in situ preparation, the phosphorus ligand/transition metal compound ratio (mol/mol; P/Pd) amounts to about 0.1:1 to 100:1, preferably to about 6:1 to 15:1. Suitable phosphine ligands are for example chiral and non-chiral mono- and diphosphorus compounds such as are described in Houben-Weyl, Methoden der organischen Chemie, volume E1, page 106 et. seq. Georg Thieme Verlag Stuttgart, 1982, and Aspects Homog. Catal., 4,145–202 (1981), especially those described above.

For the in situ preparation of the palladium-phosphine complex compound palladium-(II) chloride or palladium-(II) acetate, palladium-dichloro-bis(acetonitrile) and a bis (diphenylphosphino)alkane may be used.

Further, the process of the present invention comprises the use of bases for the cyclocarbonylation reaction like tertiary bases such as tri-alkyl-amines, di-aLkyl-aryl-amines, pyridines, alkyl-N-piperidines, and for example inorganic bases such as NaOH, KOH or salts of carbonic acids. Examples are (alkyl)$_3$amines, e.g. triethylamine, ethyl-diisopropyl-amine, pyridine, N-methyl-piperidine, sodium hydrogen carbonate, potassium hydrogen carbonate, di-sodium carbonate, etc. The preferred base is triethylamine. However, any base conventionally used for cyclocarbonylation can be used in the process of this invention.

Any conventional inert solvent can be used as the reaction medium. Solvents for the above reaction are known to sllaed persons. Preferred solvents are aromatic solvents, e.g. toluene, xylene, benzene, halogenated hydrocarbons, e.g. $CH_2Cl_2$, nitrites, e.g. acetonitrile, ester, e.g. ethylacetate, amides, e.g. DMF, ether, e.g. THF, dioxane, urethanes, e.g. TMU, sulfoxides, e.g. DMSO, and mixtures thereof The preferred solvent is toluene.

In carrying out the cyclocarbonylation reaction any of the conditions conventionally employed in carrying out such reaction can be utilized in accordance with this invention. This reaction is carried out so that one mole of carbon monoxide is reacted with one mole of the compound of formula II to produce the cyclocarbonylated reaction product which reaction product is the carboxylic acid ester of the compound of formula I. This reaction is carried out by introducing carbon monoxide into the reaction medium. In carrying out this reaction, usually a stoichiometric excess of carbon monoxide is added to the reaction medium to ensure complete reaction. This is achieved by adjusting the pressure of the carbon monoxide added. By utilizing the conventional reaction conditions for such cyclocarbonylation reaction, one achieves the formation of the reaction product of one mole of the carbon monoxide with one mole of the compound of formula II above. The reaction product formed from this reaction is not isolated from the reaction medium but is treated with a base to remove the ester group from the hydroxy moiety on the compound of formula I and form the compound of formula I. In the cyclocarbonylation reaction, the temperature can vary between 40° C. and 170° C., preferably between 60–120° C., and most preferably the reaction is performed at about 90° C. The substrate/catalyst ratio (mol/mol; S/Pd) amounts to 1 to 10000, preferably 100 to 5000, more preferably 1000 to 2000 and most preferably 1200 to 1500. For the in situ preparation, the above mentioned phosphorus ligand/transition metal compound ratio (mol/mol; P/Pd) amounts to 0.1:1 to 100:1, preferably 6:1 to 15:1. The upper limit for the carbon monoxide (CO) pressure is only limited by the specification of the autoclave used. For the lower pressure limit the carbonylation reaction would work even with a CO pressure of 1 bar. Preferably, the CO pressure is about 20 to 70 bar, more preferably 35 to 60 bar.

The cydocarbonylation reaction of this invention is carried out in the presence of a base and a carboxylic acid anhydride to form the carboxylic acid ester of the compound of formula I. Any conventional carboxylic acid anhydride can be used, particularly the aroic acid anhydrides and the lower alkanoic acid anhydrides. Among the preferred carboxylic acid anhydrides are benzoic acid anhydride and acetic acid anhydride with acetic acid anhydride being particularly preferred. The carboxylic acid anhydride should be present in the reaction medium in sufficient quantity to allow it to react, during the cyclocarbonylation reaction, with all of the compounds of formula II present in this reaction medium. However, a stoichiometric excess of the carboxylic acid anhydride can be present in the reaction medium.

Surprisingly it has been found that the "cruder" compound of Formula II can be used for the preparation of the compound of Formula I. A preparation of a crude material is performed by collecting the compound of Formula II, e.g. 1-(2-thienyl)allyl acetate, with an organic solvent and drying without further purification. The preparation of this material is exemplified in Example 1. Example 2B shows the use of the crude starting material for the preparation of the compound of Formula I.

The cyclocarbonylation reaction is followed by saponification. Conditions for saponification reactions are known in the art and described for example in "Practical Organic Chemistry", A. I. Vogel, Longmans Ed., 1967, p. 390–393. In carrying the saponification reaction of the carboxylation acid ester of formula I, the reaction medium in which this reaction product is formed is treated with a base. Any conventional base can be utilized. Normally, it is preferred to utilize the alkali metal or alkaline earth metal bases such as alkali metal, hydroxides, alkoxides, etc. In a preferred embodiment of the present invention, the saponification is carried out in a biphasic mixture of aqueous sodium hydroxide and toluene or in an homogeneous mixture of sodium methylate in methanol.

Compounds of Formula II may be prepared by methods known in the art, for example by reaction of a thiophene carbaldehyde of Formula III (illustrated in Scheme 2 a; commercially available, Fluka, Aldrich).

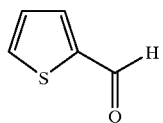

III with a vinyl-metal-X reagent, with -metal-X being —MgCl, —MgBr, —MgI or —Li, preferably — MgCl or —MgBr, followed by reaction with an acid derivative. Other allyl compounds, e.g. the corresponding allyl halogenides or allyl trialkylammonium salts, are also suitable reagents. The acid derivative can be selected from a group consisting of compounds of formulae, (R'—CO)$_2$O, R" O—(CO)—Cl, Cl—(PO)(OR")$_2$, R'—(CO)—Hal wherein R' is alkyl, perfluoro-C$_{1-20}$— alkyl, aryl, R" is alkyl, aryl or benzyl and Hal is Cl or Br. The preferred acid derivative is (R'—CO)$_2$O, and here especially the acetanhydride. The most preferred the vinyl-metal-X-reagents are vinylmagnesium chloride or vinylmagnesium bromide.

In the most preferred embodiment of the present invention, the compound of Formula II is prepared by reaction of vinylmagnesium chloride followed by reaction with acetanhydride as shown in scheme 2, variant a). Additional methods for the preparation of compound III are summarized in scheme 2.

Scheme 2

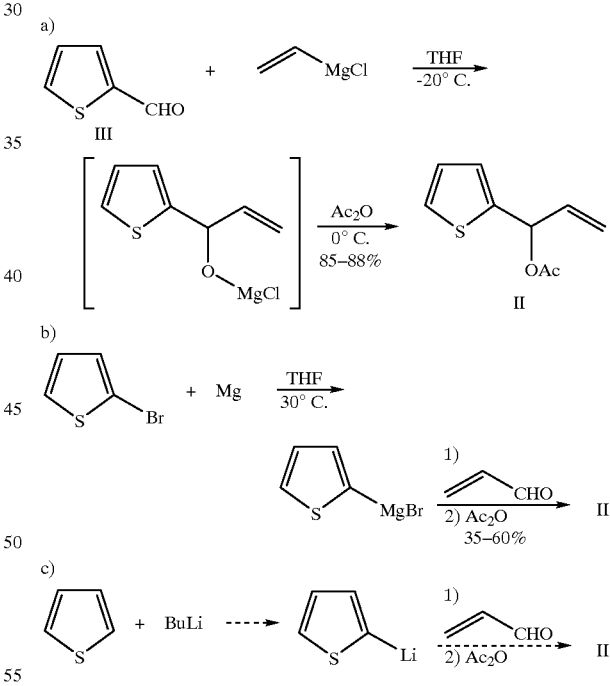

The compound of Formula I is useful for the preparation of pharmaceutically active substances, e.g. 5-[4-[2-(5-methyl-2-phenyl-4-oxazolyl)ethoxy]-7-benzothiophenylmethyl]-2,4-thiazolidinedione and its salts, especially the corresponding sodium salt A process for the preparation of this compound has been descnbed for example in International Patent Application WO 98/42704.

In addition, the compounds maybe prepared according to the following processes:

In a first step the compound of Formula I may be converted into 4-[2-(benzothiophene-4-yloxy)-ethyl]-5- methyl-2-phenyl-oxazole by reaction with a mesylate of Formula V

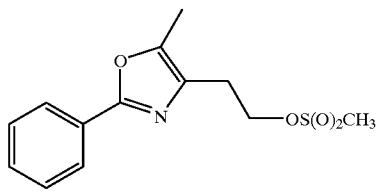

under basic conditions. The reaction may be performed in solvents like DMF with for example sodium carbonate, potassium carbonate or cesium carbonate, preferably potassium carbonate; or in THF with KtBu; or in toluene and KOH with phase transfer catalysts.

The above process maybe followed by a nitration reaction of 4-[2-(benzothiophene-4-yloxy)-ethyl]-5-methyl-2-phenyl-oxazole to give 5-methyl-4-[2-(7-nitro-benzothiophene-4-yloxy)-ethyl]-2-phenyl-oxazole. Normally nitric acid is used for the nitration reaction which may be performed at room temperature to about 50° C., preferably room temperature.

The 5-methyl-4-[2-(7-nitro-benzothiophene-4-yloxy)-ethyl]-2-phenyl-oxazole obtained by the above process maybe converted into of 5-methyl-4-[2-(7-amino-benzothiophene-4-yloxy)-ethyl]-2-phenyl-oxazole by hydrogenation. The conditions of the hydrogenation reaction ($H_2$/Raney nickel) are known in the art. Hydrogen pressure maybe 1 to 10 bar, preferably 1 bar.

The above process may be continued by the reaction of 5-methyl-4-[2-(7-amino-benzothiophene-4-yloxy)-ethyl]-2-phenyl-oxazole with HHal/$NaNO_2$ followed by reaction with CH=CHCOO$CH_3$/Cu(I)Hal, wherein Hal is Br or Cl, preferably Br. The reaction product in case of Hal is Br is methyl-2-bromo-3-[4-[2-(5-methyl-2-phenyl-oxazole-4-yl)-ethoxy]-benzothiophene-7-yl]-propionate.

The reaction of methyl-2-bromo-3-[4-[2-(5-methyl-2-phenyl-oxazole-4-yl)-ethoxy]-benzothiophene-7-yl]-propionate with thiourea will produce 2-imino-5-[4-[2-(5-methyl-2-phenyl-oxazole-4-yl)-ethoxy]-benzothiophene-7-yl]-methyl-thiazolidine-4-one. The reaction is normally performed in alkylalkohols like ethanol.

This compound (2-imino-5-[4-[2-(5-methyl-2-phenyl-oxazole-4-yl)-ethoxy]-benzothiophene-7-yl]-methyl-thiazolidine-4-one) may then be converted into 5-[7-[2-(5-methyl-2-phenyl-oxazole-4-yl)-ethoxy]-benzothiophene-4-methyl]-2,4-thiazolidinedione by reaction under acid conditions. The reaction may be performed at 1–4 bar, preferably at 1 bar. Acidic conditions are provided by an organic or inorganic acid in an appropriate solvent, e.g. HCl/ethanol.

The reaction maybe optionally continued by conversion of 5-[7-[2-(5-methyl-2-phenyl-oxazole-4-yl)-ethoxy]-benzothiophene-4-methyl]-2,4-thiazolidinedione in a corresponding salt, preferably the sodium salt (5-[7-[2-(5-methyl-2-phenyl-oxazole-4-yl)-ethoxy]-benzothiophene-4-methyl]-2,4-thiazolidinedione-Na-salt) by reaction under basic conditions, preferably with NaOH in THF.

A further embodiment of the invention comprises a process for the preparation of 5-[7-[2-(5-methyl-2-phenyl-oxazole-4-yl)-ethoxy]-benzothiophene-4-methyl]-2,4-thiazolidi-nedione and/or of 5-[7-[2-(5-methyl-2-phenyl-oxazole-4-yl)-ethoxy]-benzothiophene-4-methyl]-2,4-thiazolidinedione sodium salt comprising a) conversion of a compound of Formula I into 4-[2-(benzothiophene-4-yloxy)-ethyl]-5-methyl-2-phenyl-oxazole by reaction of a compound of Formula I

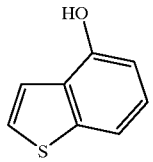

with a mesylate of Formula V

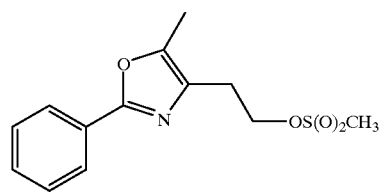

under basic conditions; followed by b) nitration of 4-[2-(benzothiophene-4-yloxy)-ethyl]-5-methyl-2-phenyl-oxazole to give 5-methyl-4-[2-(7-nitro-benzothiophene-4-yloxy)-ethyl]-2-phenyl-oxazole;

c) hydrogenation of 5-methyl-4-[2-(7-nitro-benzothiophene-4-yloxy)-ethyl]-2-phenyl-oxazole to give 5-methyl-4-[2-(7-amino-benzothiophene-4-yloxy)-ethyl]-2-phenyl-oxazole; followed by d) reaction of 5-methyl-4-[2-(7-amino-benzothiophene-4-yloxy)-ethyl]-2-phenyl-oxazole with HHal/$NaNO_2$ and CH=CHCOO$CH_3$/Cu(I)Hal, wherein Hal is Br or Cl to give methyl-$_2$-bromo-3-[4-[2-(5-methyl-2-phenyl-oxazole-4-yl)-ethoxy]-benzothiophene-7-yl]-propionate; followed by e) reaction of methyl-2-bromo-3-[4-[2-(5-methyl-2-phenyl-oxazole-4-yl)-ethoxy]-benzothiophene-7-yl]-propionate with thiourea to give 2-imino-5-[4-[2-(5-methyl-2-phenyl-oxazole-4-yl)-ethoxy]-benzothiophene-7-yl]-methyl-thiazolidine-4-one; followed by f) reaction of 2-imino-5-[4-[2-(5-methyl-2-phenyl-oxazole-4-yl)-ethoxy]-benzothiophene-7-yl]-methyl-thiazolidine-4-one under acid conditions to give 5-[7-[2-(5-methyl-2-phenyl-oxazole-4-yl)-ethoxy]-benzothiophene-4-methyl]-2,4-thiazo-lidinedione; and g) optionally followed by reaction of 5-[7-[2-(5-methyl-2-phenyl-oxazole-4-yl)-ethoxy]-benzothiophene-4-methyl]-2,4-thiazolidinedione under basic conditions to give 5-[7-[2-(5-methyl-2-phenyl-oxazole4-yl)-ethoxy]-benzothiophene-4-methyl]-2,4-thiazolidinedione-Na-salt.

The invention further comprises the use of any of the above described processes for the preparation of 5-[4-[2-(5-methyl-2-phenyl-4-oxazolyl)ethoxy]-7-benzothiophenylmethyl]-2,4-thiazolidinedione and 5-[7-[2-(5-methyl-2-phenyl-oxazole-4-yl)-ethoxy]-benzothiophene-4-methyl]-2,4-thiazolidinedione-Na-salt.

A further embodiment of the present invention comprises the compound 5-[7-[2-(5-methyl -2-phenyl-oxazole-4-yl)-ethoxy]-benzothiophene-4-methyl]-2,4-thiazolidinedione-Na-salt.

The following examples shall illustrate preferred embodiments of the present invention but are not intended to limit the scope of the invention.

EXAMPLE 1

1-(2-Thienyl)allyl Acetate

A 1.514-necked glass flask equipped with a mechanical stirrer, a thermometer and an argon inlet was charged with 112.2 g of 2-thiophenecarbaldehyde (1.00 mol) and 100 ml of THF and to the resulting solution was added dropwise at −20° C. within 1.2 h 650 ml of vinylmagnesium chloride 1.7 M solution in THF. The temperature during the addition was kept between −20 and −25° C. with aid of an acetone/dry ice bath, then increased to 0° C. during 35 min and kept at this temperature for 20 min. To the resulting brown suspension was added at ca. 0° within 40 min 132.7 g of acetic anhydride (1.30 mol). The cooling bath was removed and after stirring for 1 h 400 ml of deionized water was added at 10–15° C. within 20 min. The biphasic yellow-brown mixture was stirred for an additional 1 h at room temperature and transferred to a separatory finnel with aid of 500 ml of hexane. The brown aqueous phase was separated and extracted with 400 ml of hexane. The combined organic phases were washed with 3×200 ml deionized water, dried ($Na_2SO_4$, 15 min stirring) and rotatory evaporated ($T_{bath}35°$, 12 mbar, 1 h). Material of this quality is defined as "crude" and is also suitable for cyclocarbonylation (see Example 2B). The orange-brown oil (199.7 g) was distilled in an apparatus consisting of a 500-ml two-necked round-bottomed flask, a distillation head with water-cooling and a fraction sampler. A forerun containing low-boiling components (yellowish oil) was collected at $T_{head}$ between room temperature and 55° C. and 0.5–0.6 mbar, the main fraction was collected at $T_{head}$ of 59–62° C. ($T_{pot}$63–67° C.) and 0.4 mbar. Yield: 161.53 g (88.6%) of 1-(2-thienyl)allyl acetate as a slightly yellow oil.

EXAMPLE 2A

4Hydroxybenzothiophene

An autoclave was charged under an argon flow with 27.34 g of 1-(2-thienyl)allyl acetate (0.150 mol, distilled), 28.4 ml of acetic anhydride (30.6 g, 0.30 mol), 42.0 ml of triethylamine (30.7 g, 0.30 mol), 23.6 mg of palladium acetate (0.105 mmol) and 0.264 g of triphenylphosphine (1.00 mmol), all with aid of 53 ml of toluene. Then the autoclave was sealed, evacuated twice under slow stirring (150 rpm) to 0.2 bar and pressurized with 8 bar of argon, then pressurized three times with 20 bar of carbon monoxide and vented, and finally pressurized with 50 bar of carbon monoxide. The reaction mixture was stirred (500 rpm) and heated at 120° C. and the carbonylation carried out at 50 bar constant total pressure for 6 h. After cooling, the autoclave was vented and the CO atmosphere was exchanged by evacuating to ca. 0.2 bar and pressurizing 8 bar of argon four times. The resulting dark solution was poured into a 0.51 flask containing 120 ml of ice water and the biphasic solution was stirred for 1 h at room temperature. The aqueous phase was extracted in a separatory funnel with 80 ml of toluene and than the combined organic phases were washed with 3×30 ml, with a total of 90 ml of deionized water and reduced to a total weight of 46 g by rotary evaporation (50° C./60 mbar).

The residue containing the crude acetate was transferred to a 0.35 l glass flask under argon with aid of 25 ml of toluene. After addition of 82 ml of 4N sodium hydroxide (328 mmol) the mixture was stirred intensively (1200 rpm) at 50° for 1.5 h and then after cooling transferred in a 0.5 l separatory funnel. After removal of the organic layer, the dark aqueous phase was extracted with 80 ml of toluene and the combined organic phases were back-extracted with 2×20 ml, a total of 40 ml of deionized water. The combined aqueous phases were treated with 1.0 g of charcoal, stirred at room temperature for 5 min under argon and filtered through a Speedex layer. The filter cake was rinsed three times with 20 ml, a total of 60 ml of deionized water. The clear brown, combined phases were concentrated until no more toluene distilled, then after cooling to 5° C. in an ice bath 75 ml of 25% HCl were added under argon during 35 min, whereas the temperature was kept under 15° with aid of an ice bath. The resulting thick crystalline suspension was stirred for 1 h in an ice bath (internal temperature 2–3° C.) and filtered on a sintered glass filter. The filter cake was washed three times with 50 ml, a total of 150 ml of ice-cold water and dried on the rotavapor at 50° C./1 mbar to constant weight.

Yield: 18.9 g (84%) of 4-hydroxybenzothiophene; m.p. 76–78° C., content: 98%.

EXAMPLE 2B

4Hydroxybenzothiophene

An autodave was charged under an argon flow with 27.34 g of 1-(2-thienyl)allyl acetate (0.150 mol, crude quality, see Example 1), 28A ml of acetic anhydride (30.6 g, 0.30 mol), 42.0 ml of triethylamine (30.7 g, 30 mol), 23.6 mg of palladium acetate (0.105 mmol) and 0.264 g of triphenylphosphine (1.00 mmol), all with aid of 53 ml of toluene. Then the autoclave was sealed, evacuated twice under slow stirring (150 rpm) to 0.2 bar and pressurized with 8 bar of argon, then pressurized three times with 20 bar of carbon monoxide and vented, and finally pressurized with 50 bar of carbon monoxide. The reaction mixture was stirred (500 rpm) and heated at 120° C. and the carbonylation carried out at 50 bar constant total pressure for 6 h. After cooling, the autoclave was vented and the CO atmosphere was exchanged by evacuating to ca. 0.2 bar and pressurizing 8 bar of argon four times. The resulting dark solution was poured into a 0.51 flask containing 120 ml of ice water and the biphasic solution was stirred for 1 h at room temperature. The aqueous phase was extracted in a separatory fimnel with 80 ml of toluene and then combined organic phases were washed with 3×30 ml, a total of 90 ml of deionized water and reduced to a total weight of 46 g by rotary evaporation (50° C./60 mbar).

The residue containing the crude acetate was filtered through 17 g of silica gel (Ø=3 cm) and the filter washed with 150 ml of toluene. The combined organic phases were reduced to a total weight of 40 g by rotary evaporation and transferred to a 0.35 l glass flask under argon with aid of 20 ml of toluene. After addition of 82 ml of 4N sodium hydroxide (328 mmol) the mixture was stirred intensively (1200 rpm) at 50° for 1.5 h and then after cooling transferred in a 0.5 l separatory funnel. After removal of the organic layer, the dark aqueous phase was extracted with 80 mol of toluene and the combined organic phases were backextracted with 2×20 ml, a total of 40 ml of deionized water. The combined aqueous phases were treated with 1.0 g of charcoal, stirred at room temperature for 5 min under argon and filtered through a Speedex layer. The filter cake was rinsed three times with 20 ml, a total of 60 ml of deionized water. The clear brown, combined phases were concentrated until no more toluene distilled, then after cooling to 5° C. in an ice bath 75 ml of 25% HCl were added under argon during 35 min, whereas the temperature was kept under 15° with aid of an ice bath. The resulting thick crystalline suspension was stirred for 1 h in an ice bath (internal temperature 2–3° C.) and filtered on a sintered glass filter. The filter cake was washed three times with 50 ml, a total of 150 ml of ice cold water and dried on the rotavapor at 50° C./1 mbar to constant weight.

Yield: 16.5 g (73%) of 4-hydroxybenzothiophene as brown crystals; m.p. 75–76° C., content: 95%.

EXAMPLE 3

Variation of Phosphorus Ligands 4.93 mg of palladium acetate and 57.57 mg of triphenylphosphine in 10 ml of toluene were stirred for 1 h in a glove-box ($O_2$ 21 l ppm). A 35 ml autoclave was charged with 0.40 g of distilled 1-(2-thienyl)allyl acetate, 0.42 ml of acetanhydride, 0.62 ml of triethylamine and 1.0 ml of the catalyst solution described above. The autodave was conditioned with 30 bar of CO and pressurized with 70 bar of CO. The cyclocarbonylation was carried out at 120° C. for 2 h. GC-analysis revealed a conversion of 96% with a content of 4-acetoxybenzthiophene of 91%.

A) Examples 3.1–3.6:

According to Example 3, table 1 summarizes the following experiments which were performed with phosphorus ligands other then triphenylphosphine.

TABLE 1

| Example | p-ligand[b] | % conversion[a] | % Content of 4-Acetoxybenzothiophene[a] |
|---|---|---|---|
| 3.1 | PPh(3,5-tBu-Ph)$_2$ | 92 | 87 |
| 3.2 | P(3,5-tBu-Ph)$_3$ | 93 | 88 |
| 3.3 | AMPHOS | 99 | 95 |
| 3.4 | NMDPP | 98 | 94 |
| 3.5 | P(2-Furyl)$_3$ | 96 | 90 |
| 3.6 | P(o-DMA-Ph)$_3$[c] | 13 | 12 |

[a]Determined via GC (area-%).
[b]See structures in Scheme 1.
[c]P/Pd = 2

B) Examples 3.7–3.23:

The following additional examples 3.7 to 3.23 were performed with further phosphorus ligands. The reaction were performed according to the description given above. However, the autoclave was pressurized with 50 bar CO and the cyclocarbonylation reaction was carried out at 90° C. for 16–18 h.

TABLE 2

| Example No. | p-Ligand[b] | P/Pd[c] | % conversion[a] | % Content[a] |
|---|---|---|---|---|
| 3.7 | PPh(3,5-tBu-Ph)$_2$ | 2 | >99 | 94 |
| 3.8 | P(3,5-tBu-Ph)$_3$ | 2 | >99 | 97 |
| 3.9 | PAMP | 2 | >99 | 92 |
| 3.10 | MOP | 2 | >99 | 92 |
| 3.11 | P(2-Furyl)$_3$ | 10 | >99 | 85 |
| 3.12 | TROPP-Ph | 6 | >99 | 95 |
| 3.13 | PPh(Diphol) | 6 | >99 | 88 |
| 3.14 | (S,S)-DDPPI | 2 | >99 | 92 |
| 3.15 | DPEphos | 2 | 99 | 40 |
| 3.16 | DPPM | 2 | 40 | 30 |
| 3.17 | DIOP | 4 | 99 | 72 |
| 3.18 | P(O-nC$_4$H$_9$)$_3$ | 6 | 99 | 86 |
| 3.19 | Diphol-DIOP | 2 | 99 | 71 |
| 3.20 | DPPF | 2 | >99 | 81 |
| 3.21 | TPP-ox-Ph | 1 | 85 | 44 |

TABLE 2-continued

| Example No. | p-Ligand[b] | P/Pd[c] | % conversion[a] | % Content[a] |
|---|---|---|---|---|
| 3.22 | P(m-Tol)$_3$ | 6 | >99 | 83 |
| 3.23 | P(n-Bu)$_3$ | 6 | 95 | 70 |

[a]% Content of 4-acetoxybenzothiophene, determined via GC (Area %).
[b]See structures in Scheme 1.
[c]Phosphorus-to-palladium molar ratio.

EXAMPLE 4

Cyclocarbonylation reactions: CO pressure and S/Pd ratio 6.0 g of distilled 1-(2-thienyl)allyl acetate were reacted for 4 h as described in Example 2 A with 6.2 mg of palladium acetate, 72.1 mg of triphenylphosphine, 6.3 ml of acetanhydride and 9.3 ml of triethylamine present GC-analysis revealed a conversion of 98% with a content of e-acetoxybenzthiophene of 94%.

Examples 4.1–4.7:

According to Example 4 table 2 summarizes experiments performed under different reaction conditions (CO pressure and S/Pd ratio).

TABLE 2

| | | | | % yield[b] | | |
|---|---|---|---|---|---|---|
| Example No. | P$_{co}$ [bar][a] | S/Pd | T [° C.] | 2 h | 4 h | 6 h |
| 4.1 | 70 | 1200 | 120 | 99 | — | — |
| 4.2 | 70 | " | 100 | 90 | 98 | n.d. |
| 4.3 | 40 | " | 120 | 96 | 99 | >99 |
| 4.4 | 20 | " | " | 67 | 88 | 89 |
| 4.5 | 70 | 1500 | " | 97 | >99 | — |
| 4.6 | 50 | " | " | n.d. | n.d. | >99 |
| 4.7 | 40 | " | " | 92 | 97 | 98 |

[a]determined at RT.
[b]Determined via GG (area-%).

EXAMPLE 5

4-[2-(Benzothiophene-4-yloxy)-ethyl]-5-methyl-2-phenyl-oxazole 218 g (1.45 mol) of 4-hydroxy-benzothiophene and 511 g (1.82 mol) of mesylate of Formula V

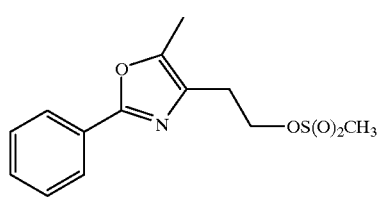

V were dissolved in 5.4 l of DMF, followed by addition of 555 g (4.02 mol) of potassium carbonate (dry). The reaction mixture was stirred at 100 to 105° C. for 6 to 8 hours. The resulting suspension was cooled to 5° C. and 7 l of water was added. The suspension was stirred at 5° C. for 30 minutes. The precipitate was filtered with suction and washed with 550 ml of DMF/water (1:1) and 1,1 1 water. The precipitate was stirred at 0 to 5° C. in 1 l of MEK (methylethylketone) for 30 minutes. Then the precipitate was filtered with suction and dried at 50° C.

Yield: 365 g (=75%) 4-[2-(benzothiophene-4-yloxy)-ethyl]-5-methyl-2-phenyl-oxazole; m.p.126° C./129–131° C.

EXAMPLE 6

5-Methyl-4-[2-(7-nitro-benzothiophene-4-yloxy)-ethyl]-2-phenyl-oxazole 286 g (0.853 mol) of 4-[2-(benzothiophene-4-yloxy)-ethyl]-5-methyl-2-phenyl-oxazole were suspended in 6.3 l of glacial acetic acid. Temperature was raised to 60° C. The resulting clear solution was cooled to 25° C. 132 ml (3.18 mol) of 100% nitric acid were added within 3 minutes. The reaction miture was cooled below 30° C. After crystallization the suspension was stirred at 18 to 20° C. for 1 hour. The precipitate was filtered with suction and washed with 2×600 ml of tert-butyl methyl ether. The residue was suspended in 4 l of acetic ester for 15 minutes. 200 g (1.9 mol) of sodium carbonate in 3 l water were added. The resulting suspension was stirred for 1 hour. Acetic ester was distilled off followed by addition of 2 l of water. The suspension was stirred for 30 minutes. The precipitate was filtered with suction, washed with water and dried (50° C., 24 hours).

Yield: 210 g of 5-methyl-4-[2-(7-nitro-benzothiophene-4-yloxy)-ethyl]-2-phenyl-oxazole (=70%); m.p. 149–151° C.

EXAMPLE 7

5-Methyl-4-[2-(7-amino-benzothiophene-4-yloxy)-ethyl]-2-phenyl-oxazole 50 g (1.052 mol) of 5-methyl-4-[2-(7-nitro-benzothiophene-4-yloxy)-ethyl]-2-phenyl-oxazole were solved in 1 l of THF at 20 to 25° C. 75 ml Lewatit M 600 (OH_form) (Bayer AG) were washed with about 100 ml THF, added to the 5-methyl-4-[2-(7-nitro-benzothiophene-4-yloxy)-ethyl]-2-phenyl-oxazole solution and stirred at room temperature for 1 hour. Then the Lewatit M 600 material was filtered with suction and washed with 100 ml THF. 12.5 g of Raney nickel were added to the combined THF solutions followed by hydrogenation of the 5-methyl-4-[2-(7-nitro-benzothiophene-4-yloxy)-ethyl]-2-phenyl-oxazole at standard pressure. The temperature of the reaction mixture should not exceed 35 to 40° C. Hydrogen pressure was increased to 6 bar within 6 hours. After hydrogenation the reaction mixture was stirred for 1 hour. Then the catalyst was filtered with suction, the THF was distilled off, 180 ml ethanol was added and the residue was boiled out for 30 minutes. The reaction mixture was stirred at 0° C. for 1 hour. The precipitate was filtered with suction and the residue was washed with 25 ml ethanol and dried for 24 hours at 50° C. (vacuum).

Yield: 42.4 g of 5-methyl-4-[2-(7-amino-benzothiophene-4-yloxy)-ethyl]-2-phenyl-oxazole (=92%). m.p. 122–126° C.

EXAMPLE 8

Methyl-2-bromo-3-[4-[2-(5-methyl-2-phenyl-oxazole-4-yl)-ethoxy]-benzothiophene-7-yl]-propionate 320 g (0.91 mol) of 5-methyl-4-[2-(7-amino-benzothiophene-4-yloxy)-ethyl]-2-phenyl-oxazole were solved in 6.4 l acetone. Within 30 sec one third of a 320 ml (2.74 mol) of 48% HBr in 900 ml water were added. After cooling to 0 to 4° C. and crystallization the suspension was stirred at 0 to 4° C. for 1 hour. Then the remaining 48% HBr solution in water was added within 15 minutes at 0 to 4° C. and stirred at this temperature for 15 minutes followed by addition of 63.9 g (0.93 mol) sodium nitrite in 180 ml water within 15 minutes at 3 to 5° C. and stirring for 30 minutes at 3 to 5° C. 1230 ml of methacrylate $CH=CHCOOCH_3$ (13.6 mol) was added to this reaction mixture at 10 to 14° C. followed by addition of 3.2 g Cu(I)bromide. Temperature was increased to 20 to 25° C. within 30 minutes followed by stirring at this temperature for 1 hour and 10 minutes at 30° C. 1.8 l of water was added to the reaction mixture followed by distillation of acetone/methacrylate $CH=CHCOOCH_3$ at a temperature of 40° C. The final volume was about 21.1 l of water was added to separate the remaining methacrylate $CH=CHCOOCH_3$. The final volume was about 2 l. The black precipitate was solved by addition of 4.5 l of acetic ester and stirring for 15 minutes. The two phase reaction mixture was filtered and the aqueous phase was extracted with 2 l of acetic ester. After extraction with 2 l of an aqueous 2% NaCl-solution the acetic ester solutions were combined and distilled. 2 l of acetic ester was added to the residue and again distilled. 3 l of ethanol were added to the residue and boiled. 15 g of activated charcoal were added and stirred for 15 minutes. After filtration and cooling to room a precipitate was formed. The suspension was stirred for 1 hour at room temperature and an additional hour at 0° C. After washing with cold ethanol the precipitate was dried for 24 hours at 50° C. (vacuum).

Yield: 310 g of methyl-2-bromo-3-[4-[2-(5-methyl-2-phenyl-oxazole-4-yl)-ethoxy]-benzothiophene-7-yl]-propionate (=68%); m.p. 97 to 99° C.

EXAMPLE 9

2-Imino-5-[4-[2-(5-methyl -2-phenyl-oxazole-4yl)-ethoxy]-benzothiophene-7-yl]-methyl-thiazolidine-4-one 190 g (0.380 mol) of 5-methyl-4-[2-(7-amino-benzothiophene-4-yloxy)-ethyl]-2-phenyl-oxazole were suspended in 2.85 l of ethanol. 31.6 g (0.415 mol) of thiourea and 34.8 g of sodium acetate were added. After boiling for about 18 hours (reflux) the reaction mixture was cooled to 0 to 4° C. and stirred for 1.5 hours at this temperature. The precipitate was filtered with suction and washed twice with 250 mnl cold ethanol. 1.9 l of water was added to the residue, the mixture was stirred for 10 minutes and the precipitate was filtered with suction and dried for 24 hours at 80° C. (vacuum).

Yield: 147 g of 2-imino-5-[4-[2-(5-methyl-2-phenyl-oxazole-4-yl)-ethoxy]-benzothiophene-7-yl]-methyl-thiazolidine-4-one (84%); m.p: 224–227° C.

Example 10

5-[7-[2-(5-Methyl-2-phenyl-oxazole-4-yl)-ethoxy]-benzothiophene-4-methyl]-2,4-thiazolidinedione 283.3 g (0.61 mol) of 2-imino-5-[4-[2-(5-methyl-2-phenyl-oxazole-4-yl)-ethoxy]-benzothiophene-7-yl]-methyl-thiazolidine-4-one were suspended in 2.83 l ethanol. 2.83 l of 2 N hydrochloric acid were added. The resulting suspension was stirred for 18 hours (reflux). The suspension was cooled for 1 hour to 0 to 4° C. and was stirred for another 2 hours at this temperature. The precipitate was filtered with suction and washed twice with 285 ml of ethanol. 2.83 l of water was added to the residue, the suspension was stirred for 30 minutes, the precipitate was filtered with suction and washed with 2 l of water. The precipitate was dried for 24 hours at 80° C. and then solved in 545 ml DMF (at 85 to 90° C.). 4.95 l of ethanol (25° C.) were added to the solution. The resulting suspension was stirred for 2 hours at 0 to 4° C. The precipitate was filtered with suction, washed with 270 ml of cold ethanol and dried at 80° C. for 24 hours (vacuum).

Yield: 246 g of 5-[7-[2-(5-methyl-2-phenyl-oxazole-4-yl)-ethoxy]-benzothiophene-4-methyl]-2,4-thiazolidinedione (87%); MP: 224–227° C.

EXAMPLE 11

5-[7-[2-(5-Methyl-2-phenyl-oxazole-4-yl)-ethoxy]-benzothiophene-4-methyl]-2,4-thiazolidinedione-Na-salt (5-{7-[2-(5-Methyl-2-phenyl-oxazol-4-yl)-ethoxy]-benzo[b]thiophen-4-ylmethyl}-2,4-thiazolidinedione ) (5.8 g) was dissolved in hot THF (87 ml). A solution of sodium hydroxide (0.5 g) in water (6 ml) was added, and the solution was cooled to room temperature. Another portion (87 ml) of THF was given to the solution, and after a short time a crystallization was observed. 150 ml of the solvent was distilled off in the heat. The suspension was cooled to about 0° C. and was stirred for further 2 hours. The solid was filtered and dried at 80° C.

Yield: 5.6 g of 5-[7-[2-(5-methyl-2-phenyl-oxazole-4-yl)-ethoxy]-benzothiophene-4-methyl]-2,4-thiazolidinedione-Na-salt (93%); MP: >300° C. (decomposition).

What is claimed is:

1. A process for the preparation of bicyclic compound of the formula

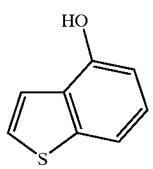

I comprising cyclocarbonylating a monocyclic compound of the formula

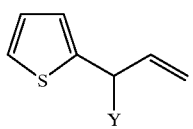

II wherein Y is halogen or —OR; and
—OR is an aryloxy group or a group of formulae —O—(CO)—R', —O—(CO)—O—R" or —O—(PO)—(OR")$_2$, wherein R' is alkyl perfluoro-$C_{1-20}$-alkyl, aryl, R" is alkyl, aryl or benzyl;
by reacting, in an organic solvent medium containing a base and a carboxylic acid anhydride, said monocyclic compound with carbon monoxide in the presence of a carbonylation catalyst capable of complexing with carbon monoxide, said cyclocarbonylation reaction being carried out by introducing carbon monoxide gas into the reaction medium to form the carboxylic acid ester of the compound of formula I and thereafter saponifying said ester formed by said carbonylation reaction by treating said ester product in said reaction medium with a base at a pH of from 8 to 14 to form said bicyclic compound.

2. The process of claim 1, wherein said cyclocarbonylation reaction is carried out in the presence of a base and a catalyst which is a complex of a transition metal compound with a ligand.

3. The process of claim 2, wherein the transition metal compound is a palladium salt or a palladium on an inert support.

4. The process of claim 3, wherein the transition metal compound is selected from a group consisting of Pd(OAc)$_2$, Pd$_2$dba$_3$, PdCl$_2$, Pd$_2$Cl$_2$(π-allyl)$_2$, PdCl$_2$(NCMe)$_2$, [Pd(NCMe)$_4$] (BF$_4$)$_2$ and Pd/C.

5. The process of claim 4, wherein the palladium compound is Pd(OAc)$_2$.

6. The process of claim 3, wherein the ligand is P(R$^1$)(R$^2$)(R$^3$) or (R$^1$)(R$^2$)P—(X)—P(R$^1$)(R$^2$) wherein R$^1$, R$^2$ and R$^3$ each independently are $C_{1-8}$-alkyl, cyclohexyl, benzyl, naphthyl, 2- or 3-pyrrolyl, 2- or 3-furyl, 2- or 3-thiophenyl, 2- or 3- or 4-pyridyl, phenyl or phenyl which is substituted by $C_{1-4}$-alkyl, $C_{1-4}$-alkoxy, halogen, trifluoromethyl, lower alkylydenedioxy or phenyl and X is binaphthyl, 6,6'-dimethyl- or 6,6'-dimethoxybiphenyl-2,2'-diyl, or one of the groups —(CH$_2$)$_n$—, —CH$_2$CH$_2$—P(C$_6$H$_5$)—, CH$_2$CH$_2$—,

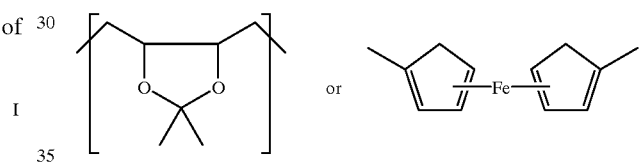

IV and n is a number from 1 to 8.

7. The process of claim 6, wherein the ligand is selected from a group consisting of triphenylphosphine, and

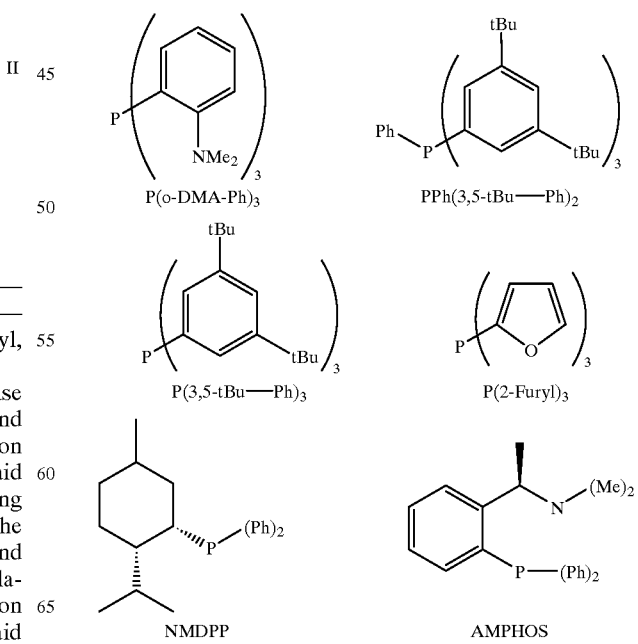

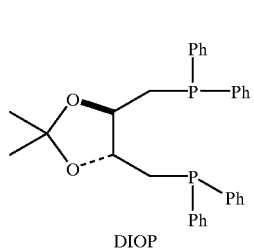
DIOP

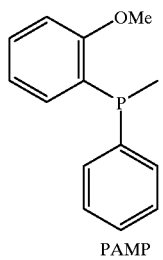
PAMP

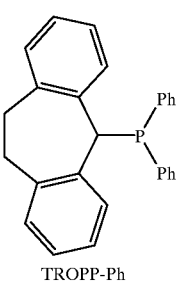
TROPP-Ph

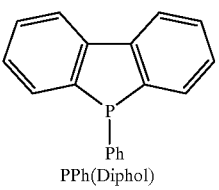
PPh(Diphol)

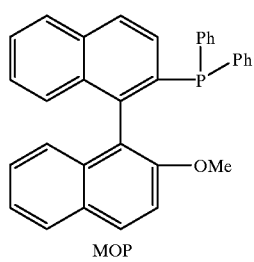
MOP and

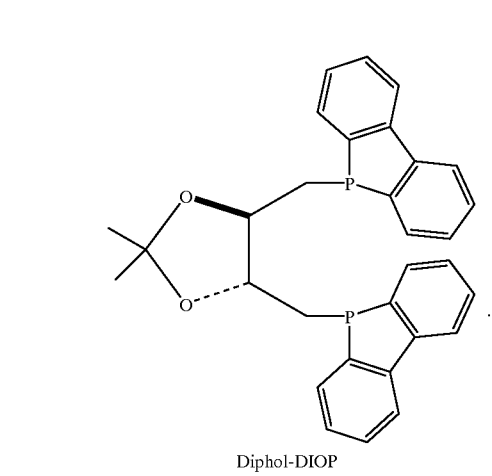
Diphol-DIOP

8. The process of claim 7, wherein the ligand is triphenylphosphine, and

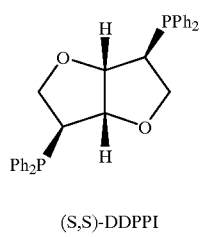
(S,S)-DDPPI

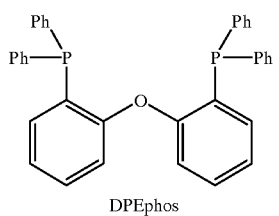
DPEphos

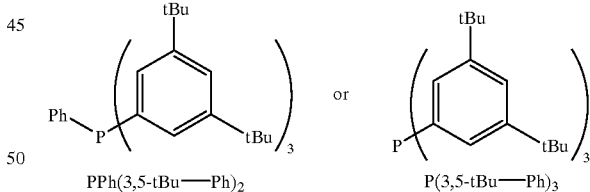
PPh(3,5-tBu—Ph)$_2$    or    P(3,5-tBu—Ph)$_3$

9. The process of claim 3 or 7, wherein the cyclocarbonylation reaction is carried out in the presence of a base selected from the group consisting of tri-alkyl-amines, di-alkyl-aryl-amines, pyridines, alkyl-N-piperidines, sodium hydroxide, potassium hydroxide and salts of carbonic acids.

10. The process of claim 3 or 7, wherein the cyclocarbonylation reaction is carried out in the presence of triethylamine.

11. The process of claim 3 or 7, wherein the saponification reaction is carried out in a biphasic mixture of sodium hydroxide in toluene or in a homogeneous mixture of sodium methylate in methanol.

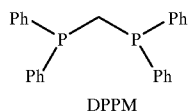
DPPM

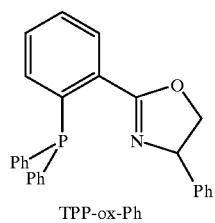
TPP-ox-Ph

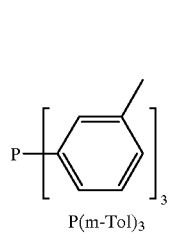
P(m-Tol)$_3$

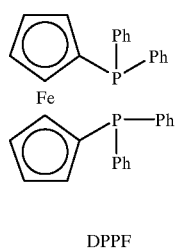
DPPF

* * * * *

UNITED STATES PATENT AND TRADEMARK OFFICE
CERTIFICATE OF CORRECTION

PATENT NO. : 6,291,685 B1
DATED : September 18, 2001
INVENTOR(S) : Junghans et al.

It is certified that error appears in the above-identified patent and that said Letters Patent is hereby corrected as shown below:

Column 9,
Lines 46-48, delete "5-[7-[2-(5-methyl-2-phenyl-oxazole-4-yl)-ethoxy]-benzothiophene-4-methyl]-2,4-thiazolidinedione"
and insert -- 5-[4-[2-(5-methyl-2-phenyl-oxazole-4-yl)-ethoxy]-benzothiophene-7-methyl]-2,4-thiazolidinedione --.
Lines 45-55, delete "5-[7-[2-(5-methyl-2-phenyl-oxazole-4-yl)-ethoxy]-benzothiophene-4-methyl]-2,4-thiazolidinedione" and
insert -- 5-[4-[2-(5-methyl-2-phenyl-oxazole-4-yl)-ethoxy]-benzothiophene-7-methyl]-2,4-thiazolidinedione --.
Lines 56-58, delete "5-[7-[2-(5-methyl-2-phenyl-oxazole-4-yl)-ethoxy]-benzothiophene-4-methyl]-2,4-thiazolidinedione-Na-salt" and
insert -- 5-[4-[2-(5-methyl-2-phenyl-oxazole-4-yl)-ethoxy]benzothiophene-7-methyl]-2,4-thiazolidinedione --.
Lines 61-63, delete "5-[7-[2-(5-methyl-2-phenyl-oxazole-4-yl)-ethoxy]-benzothiophene-4-methyl]-2,4-thiazolidinedione" and
insert -- 5-[4-[2-(5-methyl-2-phenyl-oxazole-4-yl)-ethoxy]-benzothiophene-7-methyl]-2,4-thiazolidinedione --.
Lines 63-65, delete "5-[7-[2-(5-methyl-2-phenyl-oxazole-4-yl)ethoxy]-benzothiophene-4-methyl]-2,4-thiazolidinedione-Na-salt" and
insert -- 5-[4-[2-(5-methyl-2-phenyl-oxazole-4-yl)-ethoxy]benzothiophene-7-methyl]-2,4-thiazolidinedione --.

Column 10,
Lines 46-48, delete "5-[7-[2-(5-methyl-2-phenyl-oxazole-4-yl)-ethoxy]-benzothiophene-4-methyl]-2,4-thiazolidinedione" and
insert -- 5-[4-[2-(5-methyl-2-phenyl-oxazole-4-yl)-ethoxy]-benzothiophene-7-methyl]-2,4-thiazolidinedione --.
Lines 49-51, delete "5-[7-[2-(5-methyl-2-phenyl-oxazole-4-yl)-ethoxy]-benzothiophene-4-methyl]-2,4-thiazolidinedione" and
insert -- 5-[4-[2-(5-methyl-2-phenyl-oxazole-4-yl)-ethoxy]-benzothiophene-7-methyl]-2,4-thiazolidinedione --.
Lines 52-54, delete "5-[7-[2-(5-methyl-2-phenyl-oxazole-4-yl)-ethoxy]-benzothiophene-4-methyl]-2,4-thiazolidinedione-Na-salt" and
insert -- 5-[4-[2-(5-methyl-2-phenyl-oxazole-4-yl)-ethoxybenzothiophene-7-methyl]-2,4-thiazolidinedione --.

UNITED STATES PATENT AND TRADEMARK OFFICE
CERTIFICATE OF CORRECTION

PATENT NO.    : 6,291,685 B1
DATED         : September 18, 2001
INVENTOR(S)   : Junghans et al.

It is certified that error appears in the above-identified patent and that said Letters Patent is hereby corrected as shown below:

Column 10, cont'd,
Lines 58-60, delete "5-[7-[2-(5-methyl-2-phenyl-oxazole-4-yl)-ethoxy]-benzothiophene-4-methyl]-2,4-thiazolidinedione-Na-salt" and
insert -- 5-[4-[2-(5-methyl-2-phenyl-oxazole-4-yl)-ethoxy]benzothiophene-7-methyl]-2,4-thiazolidinedione --.
Lines 62-64, delete "5-[7-[2-(5-methyl-2-phenyl-oxazole-4-yl)-ethoxy]-benzothiophene-4-methyl]-2,4-thiazolidinedione-Na-salt" and
insert -- 5-[4-[2-(5-methyl-2-phenyl-oxazole-4-yl)-ethoxy]benzothiophene-7-methyl]-2,4-thiazolidinedione --.

Column 16,
Lines 55-56, delete "5-[7-[2-(5-methyl-2-phenyl-oxazole-4-yl)-ethoxy]-benzothiophene-4-methyl]-2,4-thiazolidinedione" and
insert -- 5-[4-[2-(5-methyl-2-phenyl-oxazole-4-yl)-ethoxy]-benzothiophene-7-methyl]-2,4-thiazolidinedione --.

Column 17,
Lines 8-10, delete "5-[7-[2-(5-methyl-2-phenyl-oxazole-4-yl)-ethoxy]-benzothiophene-4-methyl]-2,4-thiazolidinedione" and
insert -- 5-[4-[2-(5-methyl-2-phenyl-oxazole-4-yl)-ethoxy]-benzothiophene-7-methyl]-2,4-thiazolidinedione --.
Lines 13-15 delete "5-[7-[2-(5-methyl-2-phenyl-oxazole-4-yl)-ethoxy]-benzothiophene-4-methyl]-2,4-thiazolidinedione-Na-salt" and
insert -- 5-[4-[2-(5-methyl-2-phenyl-oxazole-4-yl)-ethoxy]benzothiophene-7-methyl]-2,4-thiazolidinedione --.

UNITED STATES PATENT AND TRADEMARK OFFICE
CERTIFICATE OF CORRECTION

PATENT NO.   : 6,291,685 B1
DATED        : September 18, 2001
INVENTOR(S)  : Junghans et al.

It is certified that error appears in the above-identified patent and that said Letters Patent is hereby corrected as shown below:

Column 17, cont'd,
Lines 16-17 delete "5-[7-[2-(5-methyl-2-phenyl-oxazole-4-yl)-ethoxy]-benzothiophene-4-methyl]-2,4-thiazolidinedione" and
insert -- 5-[4-[2-(5-methyl-2-phenyl-oxazole-4-yl)-ethoxy]-benzothiophene-7-methyl]-2,4-thiazolidinedione --.
Lines 26-28 delete "5-[7-[2-(5-methyl-2-phenyl-oxazole-4-yl)-ethoxy]-benzothiophene-4-methyl]-2,4-thiazolidinedione-Na-salt" and
insert -- 5-[4-[2-(5-methyl-2-phenyl-oxazole-4-yl)-ethoxy] benzothiophene-7-methyl]-2,4-thiazolidinedione --.

Signed and Sealed this

Twenty-fifth Day of March, 2003

JAMES E. ROGAN
*Director of the United States Patent and Trademark Office*